United States Patent
Jager

(10) Patent No.: US 6,592,880 B1
(45) Date of Patent: Jul. 15, 2003

(54) METHOD FOR INHIBITION OF SORBATE-INDUCED BROWN DISCOLORATIONS IN COSMETIC COMPOSITIONS AND FOODSTUFFS

(75) Inventor: Martin Jager, Offenheim (DE)

(73) Assignee: Aktiengesellschaft (DE)

( * ) Notice: Subject to any disclaimer, the term of this patent is extended or adjusted under 35 U.S.C. 154(b) by 862 days.

(21) Appl. No.: 08/894,193

(22) PCT Filed: Feb. 5, 1996

(86) PCT No.: PCT/EP96/00468

§ 371 (c)(1),
(2), (4) Date: Aug. 14, 1997

(87) PCT Pub. No.: WO96/25140

PCT Pub. Date: Aug. 22, 1996

(30) Foreign Application Priority Data

Feb. 15, 1995 (DE) .......................................... 195 04 999

(51) Int. Cl.⁷ ................................................ A61K 7/00
(52) U.S. Cl. ...................................................... 424/401
(58) Field of Search ................ 424/401, 439; 514/390

(56) References Cited

U.S. PATENT DOCUMENTS 5,482,965 A * 1/1996 Rajadhaksha ................ 514/452

FOREIGN PATENT DOCUMENTS

| DE | 158357 | 1/1983 |
| JP | 5-339135 | * 12/1993 |

* cited by examiner

Primary Examiner—Theodore J. Criares
(74) Attorney, Agent, or Firm—Connolly Bove Lodge & Hutz LLP

(57) ABSTRACT

Method for inhibition of sorbate-induced brown discolorations in cosmetic compositions and foodstuffs, and color-stabilized formulations containing sorbate preservative.

The invention relates to a method for visual and sensorial stabilization of foodstuffs and cosmetic compositions containing sorbate preservative, which comprises adding allantoin or allantoin and citrates to these products as browning inhibitors.

18 Claims, No Drawings

METHOD FOR INHIBITION OF SORBATE-INDUCED BROWN DISCOLORATIONS IN COSMETIC COMPOSITIONS AND FOODSTUFFS

Method for inhibition of sorbate-induced brown discolorations in cosmetic compositions and foodstuffs, and color-stabilized formulations containing sorbate preservative.

The invention relates to a method for the preparation of color-stabilized cosmetic compositions and foodstuffs containing sorbate preservative and to these compositions themselves.

Sorbic acid (2,4-hexadienoic acid) and its salts, in particular the readily water-soluble potassium salt, have been used worldwide for many years for preserving food-stuffs. Sorbic acid is an unsaturated fatty acid which is distinguished by particular physiological tolerability. Sorbic acid is metabolized in the human body analogously to a fatty acid, is not accumulated and is classified as safe by the scientific advisory committees of the World Health Organization and of the European Union. The ADI (acceptable daily intake) value specified for sorbic acid by both committees, which can be rated as a measure of the physiological acceptability of foodstuff additives, is 0 to 25 mg/kg of body weight and day and is therefore by far the highest ADI value of all preservatives. Sorbic acid and sorbates are regarded as non-allergenic and are therefore also not mentioned in any of the known allergy databanks (for example Leatherhead Food Tolerance Data-banks Project).

The activity of sorbic acid is directed, above all, against yeasts and molds, and to a somewhat lesser extent against bacteria. The activity of sorbic acid depends on the non-dissociated content and therefore on the pH of the goods to be preserved. Because of the high pH of 4.76, sorbic acid is also suitable for preserving weakly acid goods (to pH 6.5), in contrast to other preservatives based on organic acids.

In the solid form, sorbic acid and sorbates are stable. In aqueous solution, in foodstuffs and in cosmetic compositions, however, sorbic acid is subject to oxidative influences. In particular, aldehydes and ketones, which may be the cause of off-flavors, can be formed by oxidative cleavage of the double bonds. Polymerization products of these aldehydes, like the reaction products of these aldehydes with amino acids or other primary and secondary amino groups, can also be responsible for color changes, in particular browning reactions. Such products are called Maillard products and in many cases are responsible for color changes in cosmetic compositions and foodstuffs.

The mechanism of oxidation of sorbic acid and corresponding stabilization measures have in many cases been the subject of scientific studies (Arya, S. (1980); Stability of sorbic acid in aqueous solutions. Journal Agric. Food Chem. 28, 1246–1249; Arya. S., Thakur, B. (1988): Degradation products of sorbic acid in aqueous solutions. Food Chem. 29, 41–49; Ledward, D. (1990); Stability of sorbic acid in intermediate moisture systems. Food Add. Contam. 7, 677–683; Merciadez, M., Mohammed, K., Maniere, F. (1992): Stabilized sorbic acid or salts therefore. U.S. Pat. No. 966,246, Oct. 10, 1992; Thakur, B., Singh, R., Arya, S. (1994): Chemistry of sorbates—a basic perspective. Food Rev. Intern. 10, 71–91). In the context of the abovementioned studies, attempts have been made in some cases to reduce the sorbate-induced brown discolorations and odor changes described for foodstuffs by addition of metal ions (in particular manganese) in a concentration range of 0.1–5 ppm. In addition, color stabilization of, for example, sweetener solutions also by salts of copper, zinc and cobalt has been described. The addition of these metals, which also all have a pro-oxidative action depending on the concentration, to foodstuffs seems unacceptable physiologically. The same applies to cosmetic compositions. There therefore also continues to be the need to prevent sorbate-induced brown discolorations both in foodstuffs and in cosmetic compositions.

On the basis of their good activity against micro-organisms which spoil cosmetics and their particular skin tolerability and physiological safety, sorbic acid has recently been employed increasingly for preservation of cosmetic compositions. Sorbates are the preservatives of choice for cosmetic compositions since:

they act to a particular extent against micro-organisms which spoil cosmetics (for example Pseudomonas aeruginosa)

they prevent the formation of mycotoxins in cosmetic compositions they have a good skin and mucosa tolerability they do not irritate the skin they are not phototoxic they cause no ecological problems (water pollution class 0)

On the basis of these excellent physiological data, sorbic acid has been classified as "safe" by the CIR Expert Panel, and is approved worldwide for use in cosmetic compositions.

The technological advantages of the use of sorbate in cosmetic compositions are the following:

protection from microbial contamination during storage and use good compatibility with the raw materials of cosmetics no inactivation by the contents of cosmetics "synergistic" effects with other preservatives in cosmetics high activity at pH values relevant to cosmetics because of the favorable partition coefficient (the micro-biological sensitive aqueous phase remains), particularly suitable for preserving oil-in-water emulsions no loss of action by reaction with packaging materials On the basis of these excellent technological properties, sorbates are employed in all cosmetic compositions (for example shampoos, shower gel, body lotion, sunscreen preparations, cleansing milk, facial lotion, self-tanning compositions, decorative cosmetics, oral hygiene products and moist tissues or moist toilet paper). However, it is known from the literature that precisely in cosmetic compositions which are stored for a relatively long time, are exposed to an oxidative influence and comprise amino components, sorbate-induced brown discolorations still lead to problems (Domsch, A. (1994): Die kosmetischen Präparate [Cosmetic Preparations], volume 2: Wassrige und tensidhaltige Formulierungen [Aqueous and surfactant-containing formulations], 4th edition, page .329, Augsburg: Verlag fur die chemische Industrie). The protective measure implemented most frequently to date is the co-use of complexing agents (EDTA or citrates), which slow down sorbate-induced brown discolorations by complexing pro-oxidative metal ions. Modifications to the perfuming are a second possibility. A delay in sorbate-induced brown discolorations can be achieved by both measures. However, the problem mentioned still remains for clear formulations in clear plastic bottles (a formulation which is currently used very often) in particular. Since the brown discolorations described are temperature-dependent, this applies in particular to cosmetic compositions exported to tropical countries.

Since sorbates, because of their antimicrobial activity, can also be used as active compounds in mouthwashes, toothpastes and cleaning compositions for dentures and these products are often available as clear formulations, the use of allantoin as an active compound (anti-inflammatory, analgesic) and an inhibitor of brown discolorations caused by sorbate in oral hygiene compositions is described (Hirohata, H., Ozawa, T. (1993): Composition for dental use. JP 5–339135). However, since they generally comprise no amino components which accelerate discoloration, oral hygiene compositions do not make too high a demand on the browning-inhibiting substance.

Since degradation products of sorbic acid formed oxidatively can react to a particular extent with foodstuff constituents of high nutritional physiology value, such as amino acids, protection of sorbic acid against oxidative changes is also of considerable relevance in nutritional physiology. Studies which describe a reactivity of sorbic acid degradation products with amino acids such as lysine or glutamic acid are available (Ledward, A. D: (1990): Stability of sorbic acid in intermediate moisture systems, Food Add. Contam. 7, 677–683).

There was thus a need for a method which enables cosmetic compositions and foodstuffs to be preserved with sorbic acid without brown colorations or sensorially relevant changes occurring.

This object is achieved by a method for visual and sensorial stabilization of foodstuffs and cosmetic compositions containing sorbate preservative, which comprises adding allantoin or allantoin and citrates to these products as browning inhibitors.

The foodstuffs and cosmetic compositions containing sorbate preservative can comprise the preservative here both in the form of free sorbic acid and as physiologically acceptable salts thereof, such as, for example, potassium sorbate or calcium sorbate. The sorbate concentrations used, calculated as sorbic acid, for foodstuffs and cosmetic compositions are in general between 0.005% and 5%.

Surprisingly, sorbate-induced discolorations and odor changes in all types of cosmetic compositions can be minimized drastically by addition of allantoin, an active compound often used in cosmetics because of its anti-inflammatory, keratinolytic and wound-healing properties. If citrates (for example citric acid or disodium citrate) are additionally employed as complexing agents, sorbate-induced discolorations can be prevented virtually entirely. The usual use concentrations of sorbates in cosmetic compositions, calculated as sorbic acid, are summarized in the following table. If other preservatives for cosmetics are co-used, the concentrations are correspondingly lower.

TABLE 1

Usual use concentrations of sorbic acid in cosmetic compositions

| Product class | Type of preservation | pH | Sorbic acid concentration (in % by wt) |
|---|---|---|---|
| Shampoo | Sorbic acid | 4.8–5.5 | 0.15–0.3 |
| | Sorbic acid and others | 4.8–5.6 | <0.1–0.2 |
| Shower gel | Sorbic acid | 4.8–5.5 | <0.1–0.2 |
| | Sorbic acid and others | 4.8–5.5 | 0.15–0.35 |
| Body lotion | Sorbic acid | 5.0–6.0 | 0.1–0.2 |
| | Sorbic acid and others | 5.0–6.0 | <0.1 |
| Sunscreen milk | Sorbic acid and others | 5.2–5.6 | 0.1–0.2 |
| Cleansing milk | Sorbic acid and others | 5.8–6.2 | 0.1–0.2 |
| Facial lotion | Sorbic acid and others | 5.80 | <0.1 |
| Self-tanning composition | Sorbic acid and others | 4.90 | <0.1 |
| Decorative cosmetics | Sorbic acid and others | 6.2–7.0 | 0.1–0.2 |
| Oral hygiene | Sorbic acid | 6.5–6.6 | 0.20 |
| Moist tissues | Sorbic acid | 5.5–5.9 | 0.1–0.15 |
| | Sorbic acid and others | 5.50 | 0.10 |

Allantoin is advantageously employed in amounts of the order of 0.01 to 10% by weight, in particular 0.05 to 5% by weight, preferably 0.1 to 3% by weight, particularly preferably 0.2 to 2% by weight. For citrates, an amount of the order of 0.05 to 5% by weight, in particular 0.1 to 3% by weight, preferably 0.2 to 2% by weight and particularly preferably 0.2 to 1% by weight is recommended. Good results are achieved if the allantoin concentrations, compared with the sorbate concentrations used, are 30 to 200% by weight, in particular 40 to 150% by weight and preferably 50 to 100% by weight. Corresponding higher allantoin concentrations can be chosen for formulations which are particularly susceptible to browning. Citrates should be used in the same concentration on a percentage basis as the sorbates. If citrates are used for the purpose of pH regulation, higher concentrations can also be employed.

The invention furthermore relates to foodstuffs and cosmetic compositions containing sorbate preservative, which comprise allantoin or allantoin and citrates.

The foodstuffs and cosmetic compositions which are of particular interest here are those which comprise between 0.005 and 5% of sorbate, in particular between 0.5 and 2% by weight, preferably between 0.1 and 0.8% by weight and particularly preferably between 0.15 and 0.4% by weight (calculated as sorbic acid) and between 0.001 and 10% by weight, in particularly between 0.1 and 3% by weight, preferably between 0.2 and 2% by weight and particularly preferably between 0.2 and 1% by weight of allantoin, or between 0.001 and 10% by weight of allantoin and between 0.05 and 5% by weight, in particularly between 40 and 150% by weight and preferably between 50 and 100% by weight of citrate.

The fact that allantoin, although it contains three secondary amino groups and one primary amino group, is capable of preventing sorbate-induced discolorations in cosmetic compositions and foodstuffs seems particularly surprising. Amino groups precisely are regarded as an additional "risk factor" with respect to sorbate-induced discolorations. Furthermore, no findings that allantoin has a noticeable antioxidative potential (for example quenching of singlet oxygen or free radicals of oxygen or hydroxyl) are available from the literature. Rather, it seems that the reaction products between the sorbate degradation products and allantoin surprisingly are not colored and cause no sensorial problems. Considering the intrinsic coloration of reaction products between sorbate degradation products and amino acids, this property (colorlessness) of sorbate-allantoin adducts is particularly remarkable.

Tables 2 and 3 show the protective action of allantoin and citrates and the corresponding synergisms in aqueous solutions.

TABLE 2

Discolorations caused by sorbate in aqueous solution (40° C., up to 6 months)

| Potassium sorbate (%) | Allantoin (%) | Disodium citrate (%) | Storage time months | Extinction |
|---|---|---|---|---|
| 0.10 | — | — | 1 | 0.12 |
|  |  |  | 2 | 0.10 |
|  |  |  | 3 | 0.53 |
|  |  |  | 6 | 1.04 |
| 0.10 | 0.05 | — | 1 | 0.09 |
|  |  |  | 2 | 0.10 |
|  |  |  | 3 | 0.19 |
|  |  |  | 6 | 0.26 |
| 0.10 | 0.10 | — | 1 | 0.06 |
|  |  |  | 2 | 0.09 |
|  |  |  | 3 | 0.11 |
|  |  |  | 6 | 0.18 |
| 0.10 | — | 0.05 | 1 | 0.10 |
|  |  |  | 2 | 0.16 |
|  |  |  | 3 | 0.36 |
|  |  |  | 6 | 0.72 |
| 0.10 | — | 0.10 | 1 | 0.08 |
|  |  |  | 2 | 0.014 |
|  |  |  | 3 | 0.21 |
|  |  |  | 6 | 0.46 |
| 0.10 | 0.10 | 0.10 | 1 | 0.06 |
|  |  |  | 2 | 0.07 |
|  |  |  | 3 | 0.07 |
|  |  |  | 6 | 0.09 |

TABLE 3

Discolorations caused by sorbate in aqueous solutions (40° C., up to 6 months)

| Potassium sorbate (%) | Allantoin (%) | Disodium citrate (%) | Storage time months | Extinction |
|---|---|---|---|---|
| 0.50 | — | — | 1 | 0.20 |
|  |  |  | 2 | 0.35 |
|  |  |  | 3 | 0.81 |
|  |  |  | 6 | 1.32 |
| 0.50 | 0.50 | — | 1 | 0.12 |
|  |  |  | 2 | 0.21 |
|  |  |  | 3 | 0.29 |
|  |  |  | 6 | 0.41 |
| 0.50 | — | 0.50 | 1 | 0.18 |
|  |  |  | 2 | 0.29 |
|  |  |  | 3 | 0.43 |
|  |  |  | 6 | 0.86 |
| 0.50 | 0.50 | 0.50 | 1 | 0.06 |
|  |  |  | 2 | 0.10 |
|  |  |  | 3 | 0.16 |
|  |  |  | 6 | 0.22 |

As expected, with the addition of an amino acid, for example alanine, the discoloration of the control (without allantoin and citrates) is accelerated, while the protective action of allantoin and the synergistic mixture of allantoin and citrate is documented again (see Table 4).

TABLE 4

Discolorations caused by sorbate in aqueous solutions containing amino acid (40° C., up to 6 months)

| Potassium sorbate (%) | Allantoin (%) | Disodium citrate (%) | Alanine (%) | Storage time months | Extinction |
|---|---|---|---|---|---|
| 0.50 | — | — | 0.50 | 1 | 0.33 |
|  |  |  |  | 2 | 0.57 |
|  |  |  |  | 3 | 0.96 |
|  |  |  |  | 6 | 1.56 |
| 0.50 | 0.50 | 0.50 | 0.50 | 1 | 0.11 |
|  |  |  |  | 2 | 0.15 |
|  |  |  |  | 3 | 0.19 |
|  |  |  |  | 6 | 0.33 |

EXAMPLES

The following examples show cosmetic compositions containing sorbate preservative which have been prepared using allantoin or allantoin and citrates and stored. Corresponding controls (without allantoin or allantoin and citrate) show significantly more intensive discolorations after the same storage time and storage conditions (6 months, 40° C.).

(The INCI designations of the substances are given in parentheses in each case)

Example 1

Hair Shampoo, Clear, 16.9% WAS

|  |  | % |
|---|---|---|
| A | Na salt of alkyl-diglycol ether-sulfate (sodium laureth sulfate) liquid | 40.00 |
|  | perfume oil | 0.3 |
| B | water | 52.50 |
|  | sodium hydroxide | 0.2 |
| C | alkyl ether-carboxylic acid (laureth carboxylic acid) | 4.0 |
|  | fatty alcohol polyglycol ether (laureth-3) | 2.0 |
|  | dyestuff solution | q.s. |
|  | potassium sorbate | 0.25 |
|  | disodium citrate | 0.4 |
|  | allantoin | 0.2 |
| D | sodium chloride | 1.0 |

Preparation:
I: Stir the components of A together. II: Dissolve B, stir into I. III: Stir the components of C into I in succession. IV: If appropriate, regulate the pH. V: is Finally, adjust the viscosity with D.

Example 2

Cream Rinse

|  |  | % |
|---|---|---|
| A | dialkyldimethylammonium chloride (distearyldiammnonium chloride) | 1.5 |
|  | fatty alcohol polyglycol ether (ceteareth 3) | 1.5 |
|  | cetyl alcohol | 2.5 |

-continued

|   |   | % |
|---|---|---|
|   | paraffin oil, high-viscosity | 1.0 |
| B | alkyl-polyethoxyammonium lactate (PEG-5 stearyl-ammonium lactate | 2.0 |
|   | water | 91.00 |
|   | potassium sorbate | 0.3 |
| C | perfume oil | 0.3 |
|   | dyestuff solution | q.s. |
|   | allantoin | 0.3 |
| D | citric acid --> pH 4.0 | q.s. |

Preparation: I: Melt A at about 75° C. II: Heat B to about 75° C.
III: Add II to I, while stirring, and stir until cold.
IV: Stir the components of C into III at about 40° C. V: Adjust the pH with D.

Example 3

Washing Lotion, Clear, 10.5% WAS

|   |   | % |
|---|---|---|
| A | acylamido-polyglycol ether-sulfate Mg salt (magnesium PEG-3 cocamide sulfate) | 20.00 |
|   | acylglutamate mono-Na salt (sodium cocoyl glutamate) | 6.0 |
|   | glucamate DOE 120 | 1.0 |
|   | perfume oil | 0.3 |
|   | water | 62.40 |
|   | potassium sorbate | 0.3 |
|   | disodium citrate | 0.3 |
|   | allantoin | 0.2 |
| B | fatty acid amidoalkylbetaine (cocamidopropylbetaine) | 10.00 |

Preparation: I: Stir the components of A together. II: If necessary, regulate the pH, then adjust the viscosity with B.

Example 4

Shower Bath, 2-in-1, 18.3% WAS

|   |   | % |
|---|---|---|
| A | water | 45.90 |
|   | allantoin | 0.4 |
|   | polymer IR 400 | 0.2 |
|   | fatty acid isothionate Na salt (sodium cocoyl isothionate) | 4.0 |
| B | alkyl-diglycol ether-sulfate Na salt (sodium laureth sulfate) liquid | 30.00 |
|   | acylglutamate mono-Na salt (sodium cocoyl glutamate) | 5.0 |
|   | cetiol HE | 2.0 |
| C | alkyl ether-sulfate with pearlescence agent (sodium laureth sulfate and PEG-3 distearate) | 4.0 |
|   | perfume oil | 0.5 |
|   | fatty alcohol polyglycol ether (laureth-3) | 2.0 |
|   | fatty acid amidoalkylbetaine (cocamidopropylbetaine) | 5.0 |
|   | potassium sorbate | 0.25 |
|   | disodium citrate | 0.3 |
| D | sodium chloride | 0.7 |

Preparation: I: Dissolve the components of A, while stirring and heating at about 60° C. II: Stir B into I. Avoid foaming. III: Allow to cool and stir C in at about 35° C. IV: If appropriate, regulate pH, then adjust the viscosity with D.

Example 5

Body Lotion

|   |   | % |
|---|---|---|
| A | tallow fatty alcohol ($C_{16}$–$C_{18}$) (tallow alcohol) | 1.5 |
|   | glycerol mono-/distearate and sodium stearate (glyceryl stearate SE) | 2.0 |
|   | isopropylpalmitate | 10.00 |
|   | silicone oil (dimethicone) | 0.3 |
| B | water | 77.60 |
|   | emulsifier (sodium dihydroxycetyl phosphate and isopropyl hydroxycetyl ether) | 2.5 |
|   | carbopol (carbomer) | 0.1 |
|   | propylene 1,2-glycol | 3.0 |
|   | glycerol | 2.0 |
|   | potassium sorbate | 0.4 |
|   | allantoin | 0.5 |
| C | sodium hydroxide, 10% strength solution | 0.2 |
| D | perfume oil | 0.5 |

Preparation: Pre-swell the carbopol in water. Heat phases A and B separately to about 80° C. Add C to phase B at about 80° C. Add phase BC to phase A and emulsify (Ultra-Turrax stirrer). Stir until cold using a blade stirrer. Reduce the stirring speed as the temperature decreases. Add phase D at about 35° C. pH: 5.5.

Example 6

Sunscreen Cream, O/W Type

|   |   | % |
|---|---|---|
| A | glycerol mono-/distearate (glyceryl stearate SE) | 12.00 |
|   | cetyl/stearyl alcohol with 6 EO units (ceteareth 6 and stearyl alcohol) | 1.0 |
|   | cetyl/stearyl alcohol with 25 EO units (ceteareth 25 and stearyl alcohol) | 1.0 |
|   | caprylic/capric acid triglyceride (caprylic/capric triglyceride) | 10.00 |
|   | PPG myristyl ether (PPG-3 myristyl ether) | 10.00 |
|   | 2,4,6-trianilo-p-(certo-2'-ethylhexyl-1'-oxy)-1,3,5-triazine (octyl triazone) | 3.0 |
| B | p-aminobenzoic acid ethyl ester (PEG-25 PABA) | 5.0 |
|   | glycerol, 87% | 3.0 |
|   | potassium sorbate | 0.4 |
|   | allantoin | 0.4 |
|   | water, distilled | 55.00 |
| C | perfume oil | q.s. |

Preparation: Heat phases A and B separately to about 80° C. Stir phase B into phase A, while homogenizing, and after-homogenize briefly. Cool to about 40° C., add phase C, homogenize again.

Example 7

Dental Rinse Against Dental Plaque

| | | % |
|---|---|---|
| A | Natrosol 250 | 0.3 |
| | water, distilled | 40.00 |
| B | PEG-40 hydrogenated castor oil with 10% $H_2O$ (PEG-40 hydrogenated castor oil) | 2.5 |
| | (-)-alpha-bisabolol | 0.02 |
| | aroma oil | 0.4 |
| | ethanol, 96% | 7.5 |
| | glycerol, 87% | 8.0 |
| | allantoin | 0.4 |
| | sodium lauryl sulfate ($C_{12}$–$C_{16}$) (sodium lauryl sulfate) | 0.4 |
| | acesulfam K | 0.15 |
| | sodium bicarbonate | 1.6 |
| | potassium sorbate | 0.9 |
| | sodium salicylate | 0.4 |
| | sodium tetraborate | 0.4 |
| | water, distilled | q.s. |

Preparation: Allow phase A to swell. Dissolve phase B to give a clear solution. Stir phase A into phase B.

What is claimed is:

1. A method for visual and sensorial stabilization of a foodstuff composition, said foodstuff composition containing an amino component and a food-preserving amount of sorbic acid or at least one physiologically-acceptable sorbate salt or a combination of sorbic acid and the sorbate salt, which comprises adding a discoloration-inhibiting amount of discoloration inhibitor comprising allantoin to the foodstuff composition.

2. A method according to claim 1, wherein the preservative comprises both sorbic acid and at least one physiologically-acceptable sorbate salt.

3. A method as claimed in claim 1, wherein said food-preserving amount in the foodstuff composition, calculated as sorbic acid, ranges from 0.005 to 5% by weight.

4. A method as claimed in claim 3, wherein the discoloration-inhibiting amount ranges from 0.001 to 10% by weight.

5. A method as claimed in claim 1, wherein the discoloration-inhibiting amount ranges from 0.001 to 10% by weight.

6. A method as claimed in claim 1, wherein the amino component comprises an amino acid-containing constituent.

7. A method as claimed in claim 1, wherein the discoloration inhibitor comprises allantoin and a citrate component, wherein the citrate component is citric acid, a physiologically-acceptable citrate salt, or a combination of citric acid and the citrate salt.

8. A method as claimed in claim 7, wherein the amount of allantoin added to the foodstuff composition ranges from 0.05 to 5% by weight; and wherein the amount of citrate component added to the foodstuff composition ranges from 0.05 to 5% by weight.

9. A method as claimed in claim 6, wherein said discoloration-inhibiting amount also stabilizes the foodstuff composition against changes in sensory-detectible properties of the foodstuff composition which, absent said discoloration inhibitor, would result from interaction of the amino acid-containing constituent and degradation products of sorbic acid or a sorbate salt.

10. A method as claimed in claim 1, wherein the foodstuff composition contains a physiologically-acceptable sorbate salt.

11. A method as claimed in claim 10, wherein said sorbate salt is potassium sorbate or calcium sorbate.

12. A foodstuff composition stabilized against color changes comprising: an amino component; as at least one preservative, a food-preserving amount of sorbic acid or at least one physiologically-acceptable sorbate salt or a combination of sorbic acid and sorbate salt; and, as a discoloration inhibitor, a discoloration-inhibiting amount of allantoin.

13. A foodstuff composition as claimed in claim 12, wherein the amino component is an amino acid-containing constituent.

14. A foodstuff composition as claimed in claim 12, wherein the food-preserving amount of said preservative ranges from 0.005 to 5% by weight, calculated as sorbic acid.

15. A foodstuff composition as claimed in claim 12, wherein the discoloration inhibitor comprises allantoin and a citric component, the citric component being citric acid, a physiologically-acceptable citrate salt, or a combination of citric acid and the citrate salt.

16. A foodstuff-composition as claimed in claim 15, wherein said foodstuff composition contains 0.05 to 5% by weight of allantoin and 0.05 to 5% by weight of the citrate component.

17. A foodstuff composition as claimed in claim 13, wherein said discoloration-inhibiting amount stabilizes the foodstuff composition against changes in color and against changes in sensory-detectible properties of the foodstuff composition which, absent said discoloration inhibitor, would result from interaction of the amino acid-containing constituent and degradation products of sorbic acid or a sorbate salt.

18. A cosmetic composition stabilized against discoloration, comprising:

an amino component which accelerates discoloration, from 0.005 to 5% by weight, calculated as sorbic acid, of sorbic acid, a sorbate salt, or a combination thereof, from 0.001 to 10% by weight of allantoin, and from 0.05 to 5% by weight of citric acid, a salt thereof, or a combination thereof.

* * * * *

UNITED STATES PATENT AND TRADEMARK OFFICE
CERTIFICATE OF CORRECTION

PATENT NO.     : 6,592,880 B1
DATED          : July 15, 2003
INVENTOR(S)    : Martin Jager It is certified that error appears in the above-identified patent and that said Letters Patent is hereby corrected as shown below:

<u>Title page,</u>
Item [73], Assignee, should read -- Hoechst Aktiengesellschaft --

Signed and Sealed this

Thirtieth Day of September, 2003

JAMES E. ROGAN
*Director of the United States Patent and Trademark Office*